US005969130A

United States Patent [19]

Jennings et al.

[11] Patent Number: 5,969,130

[45] Date of Patent: Oct. 19, 1999

[54] MENINGOCOCCAL POLYSACCHARIDE CONJUGATE VACCINES

[75] Inventors: Harold J. Jennings, Gloucester; Robert Pon, Aylmer; Michele Lussier, Augustin-des Maures, all of Canada; Francis Michon, Beltsville, Md.

[73] Assignee: National Research Council of Cananda, Ottawa, Canada

[21] Appl. No.: 09/022,155

[22] Filed: Feb. 11, 1998

Related U.S. Application Data

[62] Division of application No. 08/484,569, Jun. 7, 1995, Pat. No. 5,811,102.

[51] Int. Cl.[6] .............................. C07H 5/06; C08B 37/00; C07K 1/00

[52] U.S. Cl. ................ 536/29.1; 424/194.1; 424/197.11; 424/250.1; 514/42; 514/54; 536/123.1; 530/395; 530/403

[58] Field of Search ............................ 424/197.11, 194.1, 424/250.1; 530/403, 395; 536/123.1, 29.1; 514/42, 54

[56] References Cited

U.S. PATENT DOCUMENTS

| | | | |
|---|---|---|---|
| 4,057,685 | 11/1977 | McIntire | 536/18 |
| 4,356,170 | 10/1982 | Jennings et al. | 424/92 |
| 4,619,828 | 10/1986 | Gordon | 424/92 |
| 4,644,059 | 2/1987 | Gordon | 536/1.1 |
| 4,673,574 | 6/1987 | Anderson | 424/92 |
| 4,727,136 | 2/1988 | Jennings et al. | 530/395 |
| 4,902,506 | 2/1990 | Anderson et al. | 424/92 |
| 5,425,946 | 6/1995 | Tai et al. | 424/197.11 |
| 5,576,002 | 11/1996 | Jennings et al. | 424/197.11 |

FOREIGN PATENT DOCUMENTS

| | | |
|---|---|---|
| 01 86 576 AZ | 7/1908 | European Pat. Off. . |
| 0 098 581 A3 | 1/1994 | European Pat. Off. . |
| 0 747 063 A2 | 12/1996 | European Pat. Off. . |
| WO 91/8772 | 6/1991 | WIPO . |
| WO 93/07178 | 5/1993 | WIPO . |

OTHER PUBLICATIONS

Apicella, The Journal of Infectious Diseases 140(1): 62–72 (1979), "Lipopolysaccharide–Derived Serotype Polysaccharide from Neisseria Meningitidis Group B".

Baumann, Biochemistry 32: 4007–4013 (1993), "Comparison of the Conformation of the Epitope of α (2→8) Polysialic Acid with Its Reduced and N–Acyl Derivatives".

Bundle, The Journal of Biological Chemistry 249(15): 4797–4801 (1974), "Studies on the Group–Specific Polysaccharide of Neisseria Meningitidis Serogroup X and an Improved Procedure for its Isolation".

Dick, W.E. et al. in Conjugate Vaccines, Cruse J.M. et al (eds)., Contributions to Microbiology and Immunology, New York, Karger, 1989, vol. 10, pp. 48–115.

Finne et al., The Lancet, Saturday Aug. 13, 1983, "Antigenic Similarities Between Brain Components and Bacteria Causing Meningitis".

Jennings, et al., Industrial Polysaccharides: Genetic Engineering, Structure/Property Relations and Applications, edited by M. Yalpani (1987) pp. 149–156.

Jennings et al., The Pathogenic Neisseriae, Proceedings of the Fourth International Symposium, Asilomar, California, Oct.21–25, 1984, pp. 628–632: "Enhancement of Immune Response to the Group B Polysaccharide of Neisseria Meningitidis by Means of Its Chemical Modification".

Jennings et al., The Journal of Immunology 134(4): 2651–2657 (1985), "Determinant Specificities of the Groups B and C Polysaccharides of Neisseria Meningitidis".

Jennings et al., The Journal of Immunology 137(5): 1708–1713 (1986), "Induction of Meningococcal Group B Polysaccharide–Specific IgG Antibodies in Mice by Using an N–Propionylated B Polysaccharide–Tetanus Toxoid Conjugate Vaccine".

Jennings et al., The Journal of Immunology 142(10): 3585–3591 (1989), "Unique Intermolecular Bactericidal Epitope Involving the Homosialopolysaccharide Capsule on the Cell Surface of Group B Neisseria Meningitidis and *Escherichia Coli* K1".

Jennings et al., J. Exp. Med. 165: 1207–1211 (1987): "N–Propionylanted Group B Meningococcal Polysaccharide Mimics a Unique Epitope on Group B Neisseria Meningitidis".

Jennings et al., The Journal of Immunology 127(3): 1011–1018 (1961): "Immunochemistry of Groups A, B, And C Meningococcal Polysaccharide–Tetanus Toxoid Conjugates".

Lifely et al., Carbohydrate Research 107: 187–197 (1982), "Formation and Identification of Two Novel Anhydro Compounds Obtained by Methanolysis of N–Acetylneuraminic Acid and Carboxyl–Reduced, Meningococcal B Polysaccharide".

(List continued on next page.)

*Primary Examiner*—Howard C. Lee
*Attorney, Agent, or Firm*—Morgan & Finnegan, L.L.P.

[57] ABSTRACT

The invention relates to chemically-modified group B polysaccharides of *Neisseria meningitidis*. The invention also provides vaccines in which the respective modified polysaccharides are conjugated to a protein carrier, and the like. More specifically, the present invention provides novel group B meningococcal unsaturated N-acyl derivative polysaccharides, novel conjugates of the group B meningococcal unsaturated N-acyl derivative polysaccharides, pharmaceutical compositions comprising conjugate molecules of group B meningococcal unsaturated N-acyl derivative polysaccharide fragments covalently bound to proteins, and the use of these compositions as vaccines.

9 Claims, No Drawings

OTHER PUBLICATIONS

Lifely et al., Carbohydrate Research 134: 229–243 (1984), "Rate, Mechanism, and Immunochemical Studies of Lactonisation in Serogroup B and C Polysaccharides of Neisseria Meningitidis".

Lifely et al., Carbohydrate Research 156: 123–135 (1986), "Analysis of the Chain Length of Oligomers and Polymers of Sialic Acid Isolated From Neisseria Meninitidis Group B and C *Escherichia Coli* K1 and K92".

Marburg et al., J. Am. Chem. Soc. 108: 5282–5287 (1986), "Biomolecular Chemistry of Macromolecules: Synthesis of Bacterial Polysaccharide Conjugates with Neisseria Meningitidis Membrane Protein".

Roy et al., Glycoconjuate 7: 3–12 (1990), "Efficient Synthesis of α (2–8)–Linked N–Acteyl and N–Glycoly-Ineuraminic Acid Disaccharides from Colominic Acid".

Reuter et al., Glycoconjugate 6: 35–44 (1989), "A Detailed Study of the Periodate Oxidation of Sialic Acids in Glycoproteins".

MENINGOCOCCAL POLYSACCHARIDE CONJUGATE VACCINES

This application is a continuation of Ser. No. 08/484,569, filed on Jun. 7, 1995, now U.S. Pat. No. 5,811,102.

FIELD OF THE INVENTION

This invention relates to chemically-modified group B polysaccharides of *Neisseria meningitidis*. This invention also provides vaccines in which the respective modified polysaccharides are conjugated to a protein carrier, and the like.

BACKGROUND OF THE INVENTION

Meningitis caused by group B *N. meningitidis* and *E. coli* K1 remain major world health problems. Group B meningitis occurs in both endemic and epidemic situations and accounts for approximately half of all recorded cases of meningococcal meningitis, while K1-positive *E. coli* are the leading cause of meningitis in neonates. Currently there is no vaccine commercially available against disease caused by group B meningococci and *E. coli* K1. This is in large part due to the fact that the group B meningococcal polysaccharide (GBMP) is only poorly immunogenic in humans. This poor inmmunogenicity of native GBMP and resulting immune tolerance has been postulated to be due to the presence of a common epitope in human and animal tissue. There are some recently reported candidate vaccines based on complexes of the GBMP with outer membrane proteins, but, as yet, there is no clear evidence of their efficacy in humans.

Recently, a new concept of a vaccine based on a synthetic chemically modified (N-propionylated) group B polysaccharide-protein (N-Pr-GBMP-protein) conjugate has been developed. The vaccine induces in mice high titers of IgG antibodies which are not only protective, but also cross-react with unmodified GBMP (i.e. N-acetyl-GBMP). This concept is described and claimed in U.S. Pat. No. 4,727,136, issued Feb. 23, 1988 to Harold J. Jennings, et al.

It has been inferred that a vaccine which raises cross-reactive antibodies, such as that described in U.S. Pat. No. 4,727,136, could only be successful at the expense of breaking immune tolerance. This hypothesis is legitimized by the identification of a common epitope consisting of a chain of α-(2-8)-linked sialic acid residues (with a minimum requirement of ten residues) in both the native N-Ac-GBMP and in human and animal tissue (Jennings, *Contrib. Microbiol. Immunol.* Basel, Karger, 1989, Vol. 10, 151–165). These polysialosyl chains function as developmental antigens and have for the most part been associated with the fetal state in embryonic neural cell adhesion (Finne et al, *Biochem. Biophys. Res. Commun.,* 1983, 112, 482). During post-natal maturation, this antigen is down-regulated (Friedlander et al, *J. Cell Biol.* 1985, 101, 412) but is expressed in mature humans during the regeneration of diseased muscles (Cashman et al, *Ann. Neuron.,* 1987, 21, 481) in tumor cells (Roth et al, *Proc. Natl. Acad. Sci.,* 1988, 85, 299) and in natural killer (NK) and $CD3^{+}T$ cells (Husmann et al, *Eur. J. Immunol.,* 1989, 19, 1761. Although the consequences of breaking tolerance to these fetal antigens have not yet been established, it is desirable to develop vaccines which have reduced immunogenicity for human epitopes.

Therefore, an object of the present invention is to develop modified group B meningococcal polysaccharides which are immunogenic yet induce antibodies which have reduced cross-reactivity with native epitopes of the host. It is another object to provide polysaccharide-protein conjugates which comprise these modified polysaccharides. Another object of this invention is to provide vaccines having immunogenic properties which exhibits substantially reduced cross-reactivity with GBMP.

SUMMARY OF THE INVENTION

The present invention generally provides chemically-modified group B polysaccharides of *Neisseria meningitidis*. The present invention also provides for vaccines in which the respective modified polysaccharides are conjugated to a protein carrier.

Specifically, this invention provides for unsaturated group B N-acyl derivative polysaccharides of *N. meningitidis*, conjugates of the unsaturated N-acyl derivative polysaccharide covalently bound to proteins, pharmaceutical compositions comprising conjugate molecules of *N. meningitidis* unsaturated N-acyl derivative polysaccharides, and the use of these compositions as vaccines.

In one aspect of the invention, there is provided a modified B polysaccharide of *N. meningitidis* having sialic acid residue N-acetyl ($C_2$) groups replaced by an unsaturated $C^{3-5}$ acyl group.

In another aspect, there is provided an antigenic conjugate comprising unsaturated $C_{3-5}$ N-acyl derivative polysaccharides conjugated to an immunologically suitable protein, having enhanced immunogenicity compared to native polysaccharides with reduced inducement of cross-reactive antibodies.

In a further aspect, there is provided a vaccine comprising the unsaturated N-acyl derivative polysaccharide-protein conjugate in association with a suitable carrier or diluent. The vaccines of the invention may also comprise a therapeutically effective amount of an adjuvant suitable for human use, for example aluminum phosphate, aluminum hydroxide or stearyl tyrosine.

In a yet further aspect, there is provided a method of immunizing mammals against *N. meningitidis* and *E. coli* K1 infections, which method comprises administering parenterally to mammals subject to such infections, including humans, an immunologically effective amount of the vaccine of the invention. The vaccine is typically administered in an amount of about 1 to 50 micrograms per kilogram body weight, for example 5 to 25, micrograms per kilogram body weight.

In yet another aspect, the invention provides serum and a gamma globulin fraction capable of protection against meningitis caused by group B *N. meningitidis* and *E. coli* K1. The fraction is produced by immunizing a mammal with a vaccine of the invention and preferably separating the gamma globulin fraction from the immune serum. The fraction is then administered to an individual to provide protection against or to treat on-going infection caused by the above organisms. From this, it will be appreciated that the immunogenic vaccine conjugates of the invention will be a source of therapeutic antiserum in light of their favorable immunogenicity with minimal inducement of GBMP cross-reactive antibodies. The conjugates of the invention will also be useful for raising monoclonal antibodies and, possibly, antidiotype antibodies.

We have found that most of the bactericidal and protective antibodies induced by the N-Pr-GBMP-protein conjugate described in the above-referred to Jennings et al U.S. Pat. No. 4,727,136 are not associated with the GBMP cross-reactive antibodies. In fact, most of the protective activity is contained in an N-Pr-GBMP-specific antibody population which does not cross-react with GBMP. In light of this, it is believed that the N-Pr-GBMP mimics a unique bactericidal epitope on the surface of group B meningococci.

The present invention is based on the discovery that it is possible to synthesize chemically modified GBMP's which mimic the bactericidal epitope and which, in their conjugated form, not only exhibit enhanced immunogenicity but also avoid substantially the inducement of antibodies that do cross-react with GBMP.

In arriving at the present invention, different chemically modified GBMP's have been synthesized and conjugated individually to protein, followed by injection of the conjugates into mice and the effects compared to those produced by the N-Pr-GBMP protein conjugate. Surprisingly, it has now been found that the presence of an unsaturated bond in the N-acyl results in particularly immunogenic conjugates These and other features of the invention will be better understood through a study of the following detailed description of a specific embodiment of the invention. The scope of the invention is limited only through the claims appended hereto.

DETAILED DESCRIPTION OF THE INVENTION

This invention generally provides novel group B *Neisseria meningitidis* unsaturated N-acyl derivative polysaccharides, novel conjugates of the group B unsaturated N-acyl derivatives, pharmaceutical compositions comprising conjugate molecules of group B *Neisseria meningitidis* unsaturated N-acyl derivative polysaccharide fragments covalently bound to proteins, and the use of these compositions as vaccines.

The present invention relates to group B *N. meningitidis* unsaturated N-acyl derivative polysaccharides of Formula (I):

FORMULA 1

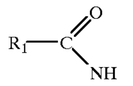

wherein $R_1$, is a $C_2$–$C_4$ unsaturated alkyl group comprising at least one double bond.

In one embodiment of the invention, $R_1$ of Formula I has three, or four carbons and two nonadjacent double bonds.

In a further embodiment of the invention, $R_1$ of Formula I is two, three, or four carbons, and the carbon most distant from the acyl carbon is bound through a double bond.

Specific, but not limiting examples of modified group B meningococcal polysaccharide N-acyl derivative polysaccharides of Formula I useful in the present invention include the following:

N-penteneoyl ($CH_2{=}CH—CH_2—CH_2—CONH—$);

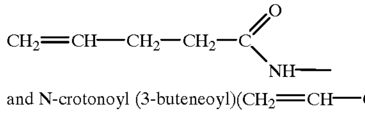

and N-crotonoyl (3-buteneoyl)($CH_2{=}CH—CH_2—CONH—$).

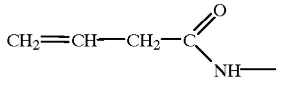

The group B meningococcal polysaccharide is isolated from *N. meningitidis* by methods which are known in the art.

In one such method, group B meningococci (strain 981B) were grown at 37° C. in a fermenter using 30 g. of dehydrated Todd Hewitt Broth (Difco Laboratories, Detroit, Mich.) per liter of distilled water. Prior to fermenter growth, the lyophilized strain was grown initially in a candle jar at 37° C. on 5% (v/v) Sheeps' Blood Agar (Difco Laboratories, Detroit, Mich.) plates. The bacteria were then transferred to 1.0 liter of Todd Hewitt Broth (as above) in an Erlenmeyer flask which was shaken at 37° C. for 7 hours at 190 r.p.m. This inoculum was then transferred to the fermenter. After fermenter growth (16 hours) the bacteria were killed by the addition of formalin to a final concentration of 0.75%. The bacteria were removed by continuous centrifugation and the group B meningococcal polysaccharide was isolated from the supernatant and purified essentially as described by Bundle et al, *J. Biol. Chem.,* 249, 4797–4801(1974) except that the protein was extracted by stirring a solution of the crude polysaccharide with cold (4° C.) 90% phenol instead of hot (50-60° C.). This latter process ensures that a high molecular weight form of the GBMP is produced.

*E. coli* (018:K1:H7) (NRCC 4283) were grown at 37° C. in a fermenter in distilled water containing dehydrated Brain Heart Infusion (BHI; 37 g/liter) (Difco Laboratories, Detroit, Mich.). Prior to fermenter growth, the lyophilized strain was grown on 50 ml of BHI solution (same as above) in an Erlenmeyer flask which was shaken at 37° C. for 7 hours at 200 r.p.m. This growth was then transferred to 1.5 liters of BHI (as above) and grown under the same conditions as described above for 7 hours. The inoculum was then transferred to the fermenter.

The procedures employed in the isolation and purification of the capsular polysaccharide of *E. coli K*1 were identical to those described above for the isolation of the group B meningococcal polysaccharide.

It will be appreciated that the isolation and purification procedures described above are not the only ones which may be utilized, and that other published procedures are available, for example those described by Watson et al, *J. Immunol,*.81, 331(1958) and in the above-mentioned U.S. Pat. No. 4,727,136.

The native polysaccharide is N-deacetylated to provide a reactive amine group in the sialic acid residue parts of the molecule. The N-deacetylation can be carried out by any known method, for example in a basic aqueous medium at elevated temperatures, for example about 90° to 110° C., and at a pH of about 13 to 14. The basic aqueous medium is suitably an aqueous alkali metal hydroxide solution, for example sodium hydroxide of about 2M concentration. Alternatively, hydrazine in aqueous solution may be used. The degree of N-deacetylation may vary from about 30% to 100% depending on the conditions. It is preferred to achieve about 90 to 100% N-deacetylation. N-deacetylated product can be recovered for example by cooling, neutralizing, purification if desired, and lyophilization.

As a result of N-deacetylation, fragments of the polysaccharide are usually produced having an average molecular weight ranging from about 3,000 to 50,000 Daltons. For use in this invention, fragments or full length polysaccharides may be used.

The N-deacetylated polysaccharide fragments or full length polysaccharides are then N-acylated to produce the corresponding N-acylated product. The N-acylation may be carried out by dissolving the N-deacetylated polysaccharide in an aqueous buffered medium having a pH of about 7.5 to 9.0, followed by adding the appropriate unsaturated acyl anhydride, optionally with an alcohol to increase solubility, and cooling to below 10° C. until the reaction is complete. If desired, the reaction medium can be purified. Non-limiting examples of purification methods which may be utilized include dialysis followed by recovery of the N-acylated product by lyophilization. The reaction is substantially complete within about 10 to 20 hours. The degree of N-acylation, as measured by analytical techniques, typically $^1H$ nmr, is at least 90% and more likely close to 100%. The N-acylation reaction does not result in any significant molecular weight reduction of the fragments.

The conjugate molecules of this invention have at least one group B *Neisseria meningitidis* polysaccharide wherein the N-acetyl group is substituted with an unsaturated N-acyl group of formula II

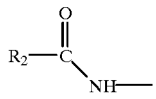

wherein $R_2$ is an unsaturated $C_{2-4}$ alkyl group. The conjugates therefore may comprise the unsaturated polysaccharides of this invention and may also include the acryloyl derivative.

It is preferred, according to the present invention, to select for conjugation purposes the $C_{3-5}$ N-acylated material having an average molecular weight corresponding to about 10 to 200 sialic acid residues. Thus, a preferred conjugate is the N-acryloyl (2-propeneoyl) derivative. This is generally achieved by way of gel filtration of the N-acylated GBMP using an Ultragel trademark AcA 44 (Bead diameter 60–140 um) column, using PBS as eluant. Alternatively, a suitable sizing membrane may be employed.

Unsaturated N-acylated material of average molecular weight of 10,000 to 40,000 Daltons, is preferably employed for the invention. This is obtained by collecting the fractions of the eluate of the column containing N-acylated GBMP material having that average molecular weight range. N-acylated material of higher average molecular weight, for example in the region of 30,000 to 40,000 Daltons, has also proved to be useful according to the invention.

The molar ratio of polysaccharide to protein in the conjugate molecules of the invention is preferably between 1 mole protein to 20 moles polysaccharide. More preferably the ratio is between 1 mole protein and about 2–15 mole polysaccharide. Most preferably the ratio is about 1 mole protein and 4 to 7 moles polysaccharide. Variations in protein/polysaccharide ratio may be achieved by adjusting the ratio of the starting components in the conjugation reaction.

In addition to providing conjugate molecules comprising unsaturated N-acyl derivative polysaccharides conjugated to protein, this invention also contemplates multivalent conjugates and their vaccines wherein different types of polysaccharides are conjugated to a single protein.

The vaccines of the invention are produced by conjugating the unsaturated N-acylated polysaccharide with an immunologically suitable carrier protein. Preferably, the carrier protein itself is an immunogen. Non-limiting examples of suitable carrier proteins are bacterial proteins, or polypeptides including tetanus toxoid, diphtheria toxoid, cross-reacting materials (CRMs), preferably $CRM_{197}$, (obtained from Sclavo Ltd., Siena, Italy), and bacterial protein carriers, such as meningococcal outer membrane proteins.

Any mode of conjugation may be employed to conjugate the modified polysaccharide fragments with the carrier protein. A preferred method is that described in U.S. Pat. No. 4,356,170, i.e. by introducing terminal aldehyde groups (via oxidation of cis-vicinal hydroxyl groups) into the N-acylated polysaccharide and coupling the aldehyde groups to the protein amino groups by reductive amination. The polysaccharide and the protein are thereby linked through a $—CH_2—$NH-protein linkage.

It is to be understood, however, that the conjugate vaccines of the invention are not limited to those produced via reductive amination. Thus, the vaccines may also be produced by conjugating the N-acylated polysaccharide with the carrier protein using an adipic dihydrazide spacer, as described by Schneerson, R., et al, Preparation, Characterization and Immunogenicity of Haemophilus influenzae type b Polysaccharide-Protein Conjugates, *J. Exp. Med.,* 1952, 361–476(1980), and in U.S. Pat. No. 4,644,059 to Lance K. Gordon. Alternatively, the binary spacer technology developed by Merck may be used, as described by Marburg, S., et al, "Biomolecular Chemistry of Macromolecules: Synthesis of Bacterial Polysaccharide Conjugates with *Neisseria meningitidis* Membrane Protein", *J. Am. Chem.* Soc., 108, 5282–5287 (1986) or, possibly, the reducing ends methodology.

The conjugate molecules prepared according to this invention typically comprise a protein to which is bound at least one meningococcal polysaccharide fragment of the present invention through a single binding site at the terminal end of the backbone of the polysaccharide fragment. Thus, this invention provides the ability, if desired, to produce meningococcal conjugate molecules wherein the polysaccharide component, except for one end, is unobscured by protein. Other methods of conjugating meningococcal polysaccharides to protein through the terminal sialic acids of the branches may, result in crosslinking, and attachment of polysaccharide to protein at a plurality of sites. This invention also contemplates conjugate molecules which may be made using a combination of methods.

The resulting N-acylated polysaccharide protein conjugates which do not possess significant cross-linking are soluble in aqueous solutions. This makes these conjugates of the invention particularly good candidates for vaccine use.

A resulting unsaturated N-acylated-polysaccharide protein conjugate of the invention has been tested in in vitro tests in mice, and has been shown to possess improved immunogenic properties as compared with the N-propionylated-polysaccharide. In addition, substantially reduced formation of cross-reactive antibodies is observed. In addition, the unsaturated conjugate demonstrated unexpected high bactericidal titers compared to other conjugates tested. In light of this, it is believed that the vaccines of the invention will be useful against meningitis caused by group B *N. meningitidis* or by *E. coli* K1 organisms. Of particular interest are vaccines for protecting human infants who are most susceptible to bacterial meningitis.

The vaccines of this invention may comprise standard carriers, buffers or preservatives known to those in the art which are suitable for vaccines. In addition, adjuvants such as alum or stearyl tyrosine may also be included in the formulation to enhance the immunogenic response.

The vaccines of the present invention are typically formed by dispersing the conjugate in any suitable pharmaceutically acceptable carrier, such as physiological saline or other injectable liquids. The administration of the vaccine of the present invention may be effected by any of the well-known methods, including, but not limited to subcutaneously, intraperitoneally or intramuscularly. The preferred method of administration of the vaccine is parenteral administration. Additives customary in vaccines may also be present, for example stabilizers such as lactose or sorbitol and adjuvants such as aluminum phosphate, hydroxide, or sulphate.

The vaccines of the present invention are administered in amounts sufficient to provoke an immunogenic response. Typically a dose of between about 1 and 50 $\mu$g polysaccharide is effective for generating such a response. Dosages may be adjusted based on the size, weight or age of the individual receiving the vaccine. The antibody response in an individual can be monitored by assaying for antibody titer or bactericidal activity and boosted if necessary to enhance the response.

A suitable dosage for the vaccine for human infants is generally within the range of about 5 to 25 micrograms, or about 1 to 10 micrograms per kilogram of body weight.

EXAMPLES

The Examples herein are meant to exemplify the various aspects of carrying out the invention and are not intended to limit the scope of the invention in any way.

Example 1

Synthesis of N-Acryloylated GBMP

Synthesis of N-acryloylated GBMP is described in Roy R. et al., *Glycoconjugate J.* (1990) 7:3–12. N-Deacteylated GBMP (150mg) was dissolved in 2.0 ml of distilled water. The solution was cooled to 0° C. and treated with 50 $\mu$l (1 eq) installments of acryloyl chloride (Aldrich Chemical Co.) for a totals of 500 $\mu$l. The pH of the solution was maintained at pH 8.5 with 4M NaOH using an autotitration unit. After the complete addition of the acid chloride (2 hr.), the pH was raised to 12 and maintained at this level for 30 minutes. The material was purified by exhaustive dialysis against distilled water at 4° C., followed by lyophilization to 163 mg. H-NMR of the material revealed 100% N-acylation with the appropriate integration pattern for the acryloyl substituent.

Example 2

Activation of N-Acryloylated GBMP

N-acryloylated GBMP (150 mg) was dissolved in distilled water (1.25 ml) followed by the addition of 3.75 ml of a 0.2M solution (~50 eq) of $NaIO_4$ in water. The solution was kept in the dark at room temperature for 1 hour, followed by the addition of ethylene glycol (400 $\mu$l, 10 eq). After 1 hour at room temperature, the solution was applied directly to a Sephadex G-10(1.6×100) column equilibrated in water (Pharmacia Fine Chemicals). The activated product was eluted off the column in the void volume peak, which was collected and lyophilized. The oxidized product was then fractionated on a BioGel A.5 column (1.6×100) (BioRad) equilibrated in phosphate buffered saline (pH 7.6). Molecular weight pools were made based on HPLC (high performance liquid chromatography) analysis (Pharmacia-Superose, 12 column) of selected fractions of the eluted material. Comparison of the relative Kav value of each fraction to a previously constructed calibration curve allowed for the selection of a discrete 11 KD fractions of oxidized acryloylated GBMP. The factions were purified by dialysis as described above. H-NMR spectroscopy of the fractionated material was consistent with oxidized N-acrylolyated GBMP.

Example 3

Preparation of a Tetanus Toxoid Conjugate of N-Acryloylated GBMP

Freshly purified tetanus toxoid monomer (TT-m; 3.5 mg) was combined in a Pierce reacti-vial with 10.5 mg of an 11 KD fraction of oxidized acryloylated GBMP. Sodium cyanoborohydride (7.0 mg) was added and the mixture was dissolved in 233 $\mu$l of phosphate buffer (0.1 M, pH 7.5). The solution was incubated at 37° C. for a total of five days. Periodically, the conjugation was monitored by size exclusion HPLC (Superose-12, Pharmacia) to visualize the shift to higher molecular weight as the conjugation progressed. The final conjugate was purified from starting materials by fractionation over a BioGel A.5 column equilibrated in PBS, followed by dialysis, and lyophilization. Colorimetric analysis for total sialic acid (Svennerholm method) and protein (BCA method, Pierce) indicated conjugates that contained between 12–30% sialic acid.

Example 4

Immunization of Mice

Typically, 10 female CF1 mice (8–10 weeks old) were immunized intraperitoneally (0.2 ml) with an amount of conjugate equivalent to 2 $\mu$g of sialic acid, with or without the addition of adjuvants such as Alum (Alhydrogel, Superfos Biosector) or RIBI's complete or component adjuvant system (RIBI Immunochem). The initial vaccination was followed by booster vaccinations on day 21 and day 35, followed by exsanguination on day 45. The blood was collected via heart puncture and the serum stored aliquoted at −86° C.

Example 5

Bactericidal Assay

The bactericidal assay was carried out in tissue culture 96 well microtiter plates (Corning). All antisera were heat inactivated at 56° C. for 30 minutes prior to their use. Group B meningococcus (strain 80–165 B:2b:p.1) was grown overnight on chocolate agar plates (QueLab) at 37° C. under a 5% $CO_2$ atmosphere, followed by inoculating a second plate and incubating it for five hours. The appropriate dilutions of antisera were made directly in the plate using Hank's balanced salt solution (HBSS) as the diluent to yield a final volume of 50 $\mu$l per well. A suspension of GBM in HBSS was made giving an O.D. ($\lambda_{580}$)=0.1 Absorbance. This suspension was diluted 40,000 times in HBSS to give the final working dilution of bacteria for the assay. Freshly thawed baby rabbit complement (Pel-Freeze Biologicals) was added (20 $\mu$l) to each well, followed by 30 $\mu$l of the working dilution of bacteria. The plate was then shaken at 37° C. for one hour. The contents of each well was mixed prior to plating (35 $\mu$l) onto chocolate agar plates. The plates were then incubated overnight at 37° C./5% $CO_2$ and the number of colony forming units (CFU) were counted. The % killing was determined relative to the mean values of either HBSS control wells or an irrelevant antiserum in the following manner:

$$\% \text{ killing}=(CFU_{control}-CFU_{antiserum}/CFU_{control})\times 100$$

Example 6

Passive Protection Assay

Mouse antisera obtained from the N-Acyl GBMP-TT immunizations were typically diluted in sterile saline or PBS (phosphate buffered saline). Groups of five female CF1 mice (8–10) weeks old were injected intravenously with 200 $\mu$l of the diluted antisera. After one hour, each group of mice was challenged with an intraperitoneal injection (500 $\mu$l; 800–1200 CFU/ml) of a suspension of Group B Neisseria meningitidis (GMB 80165 B:2b:P.1). After five hours, the blood was harvested from for the individual mice by cardiac puncture and 10 $\mu$l of the blood was plated onto chocolate agar plates. The plates were incubated at 37° C. under 5% $CO_2$ and the number of colony forming units (CFU's) were determined 15–20 hours later.

The passive protection assay is based on the reduction or clearance of bacteria in the presence of specific antibody and is measured relative to a control group lacking specific antibody. The degree of protection offered by the mouse anti-N-Acyl GBMP conjugate sera is represented by the % reduction of CFU's for each antiserum relative to an irrelevant control antiserum or PBS.

Example 7

Synthesis and Biological Activity of a Vaccine Against *Neisseria meningitidis* Serogroup B.

The new conjugate vaccine against *N. meningitidis* serogroup B was synthesized, the design of which is based on a unique modification of the native polysaccharide. The native polysaccharide (N-Ac GBMP) was derivatized at the amino terminus by complete substitution of the N-acetyl groups with N-acryloyl groups (NH—CO—CH═$CH_2$). Physical methods, such as $^1H$ and $^{13}C$-NMR spectroscopy characterized with certainty the identity and homogeneity of the new species and size exclusion HPLC demonstrated that the process did not alter the molecular size of the polysaccharide through depolymerization. Conjugates to proteins were made in a manner to similarly described procedures. Briefly, starting from preparation of the N-acryloyl GBM polysaccharide, two different lots of N-acryloyl GBMP-tetanus toxoid conjugates were prepared. Colorimetric analysis of each conjugate revealed a 13% and 20% total sialic acid to conjugate ratio, respectively. $^1$H-NMR spectroscopy of the conjugates revealed the unchanged presence of the modified polysaccharide on the protein.

In separate animal experiments, the N-Acrolyl GBMP-TT conjugates were injected into mice in conjunction with either saline, aluminum hydroxide, or RIBI's complete adjuvant (MPL+TDM+CWS) in one instance, and with RIBI's adjuvant only in the second case. The vaccines were visibly well tolerated in mice.

Serological testing of each antiserum showed that both conjugates elicited a specific response comparable or higher than those seen with N-propionyl GBMP-TT constructs using the RIBI's adjuvant system (See Table 1). Preliminary studies regarding the cross reactivity of the N-acryloyl GBMP-TT antisera showed results that were similar to the degree of cross reactivity seen with N-propionyl GBMP-TT antisera (See Table 2). One of the two lots of N-acryloyl GBMP-TT antisera showed significantly less cross reaction to the native GMBP relative to an N-propionyl GBMP-TT construct administered in the same experiment.

Both lots of N-acryloyl GBMP-TT were tested for their bactericidal activity against live GBM and have shown significant activity relative to N-propionyl GBMP-TT antisera. These results are summarized in Tables 1 and 3. The results in Table 1 are the product of a bactericidal assay performed in duplicate and are consistent with dilution values found with other assays performed with the same material. The data of Table 1 are consistent with acryloyl possessing particularly effective bactericidal activity. Table 3 compares the bactericidal activity of the two lots of N-acryloyl GBMP-TT antisera together with N-propionyl GBMP-TT antisera obtained in the same animal experiments. The assay uses a 15-fold greater number of bacteria and hence only those antisera showing strong activity were detected. From a comparison of the N-acryloyl GBMP-TT antisera to N-propionyl GBMP-TT antisera, it can be seen that the bactericidal activities are virtually equivalent.

Passive protection studies were carried out with varying dilutions, all of which demonstrated significant clearance, thus inferring protection to the mice. (See Table 1). Comparison to the N-propionyl GBMP-TT antiserum at the different dilutions gave again nearly identical results. Comparison of the two lots of N-acryloyl GBMP-TT antisera in a passive protection experiment showed that both protected the mice identically, within experimental error. (See Table 3).

TABLE 1

Summary of experiment RPV-1-63 comparing the properties of modified group B meningococcal polysaccharide-tetanus toxoid conjugates in various adjuvants

| | ELISA Titer[a] | | | Bactericidal Titer[b] | | Passive Protection Titer[c] | | |
|---|---|---|---|---|---|---|---|---|
| Antiserum | Saline | Alum | RIBI | 90% Killing | 50% Killing | % Clearance (neat) | % Clearance (1:4) | % Clearance (1:6) |
| N-Propionyl GBMP-TT | 14,387 | 38,667 | 235,456 | 210 | 690 | 100 | 81 | 73 |
| N-Butanoyl GBMP-TT | 11,253 | 38,859 | 363,264 | 9.2 | 50 | 60 | — | 0 |
| N-Penatanoyl GBMP-TT | 14,019 | 53,248 | 465,920 | 12.1 | 28 | 57 | — | 0 |
| N-Acryloyl GBMP-TT | 1,698 | 7,280 | 218,304 | 1000 | 2,120 | 96 | 78 | 46 |

[a]ELISA titer is defined as O.D. × Dilution$^{-1}$ averaged over three points on the curve. Saline, Alum, and RIBI represents the adjuvant used in the production of antisera.
[b]Reciprocal dilution of anti-modified GBMP-TT/RIBI sera required for either 50% or 90% killing of GBM 80-165. The values are accurate to +/− one dilution.
[c]% Clearance of GBM 80165 at various dilutions of anti-modified GBMP-TT/RIBI sera relative to an HBSS control.

TABLE 2

Cross reaction of the modified N-acyl GBMP-TT antisera (RPV-1-63) to native N-acetyl GBMP antigen

| | ELISA Titer[a] | | | | | | | | |
|---|---|---|---|---|---|---|---|---|---|
| | Saline | | | Alum | | | RIBI | | |
| Antiserum | N-Acyl[b] titer | N-Acyl[c] titer | Ratio of N-Acyl/ N-Acetyl titer | N-Acyl titer | N-Acetyl titer | Ratio of N-Acyl/ N-Acetyl titer | N-Acyl titer | N-Acetyl titer | Ratio of N-Acyl/ N-Acetyl titer |
| N-Propionyl GBMP-TT | 2,557 | 53 | 49 | 6,217 | 795 | 8 | 51,373 | 2,910 | 18 |
| N-Butanoyl GBMP-TT | 2,628 | 45 | 59 | 10,979 | 226 | 49 | 66,267 | 406 | 163 |
| N-Penatanoyl GBMP-TT | 2,764 | 9 | 314 | 6,491 | 150 | 43 | 120,533 | 311 | 388 |
| N-Acryloyl GBMP-TT | 338 | 7 | 46 | 3,022 | 546 | 6 | 50,040 | 1,100 | 45 |

[a]ELISA titer is defined as O.D. × Dilution$^{-1}$ averaged over three points on the curve. Saline, Alum, and RIBI represents the adjuvant used in the production of antisera.
[b]N-Acyl represents the homologous polysaccharide-Human serum albumin conjugate as coating antigen.
[c]N-Acetyl represents N-acetyl GBMP-Human serum albumin conjugate as coating antigen.

TABLE 3

Summary of the protective properties from two lots of N-Acryloyl GBMP-TT antisera relative to N-Propionyl GBMP-TT antisera

| Antiserum[a] | Bactericidal activity[b] 50% killing | Passive protection[c] % clearance |
|---|---|---|
| N-Propionyl GBMP-TT (RPV-1-45) | 53 | 92 |
| N-Acryloyl GBMP-TT (RPV-1-45) | 80 | 100 |
| N-Propionyl GBMP-TT (RPV-1-63) | 29 | 81 |
| N-Acryloyl GBMP-TT (RPV-1-63) | 100 | 78 |

[a]Antisera was raised using the RIBI's adjuvant system.
[b]Reciprocal dilution of antiserum for 50% killing of GBM 870165. Note that the assay was 15-fold greater amounts of GMB (2600 cfu/100 ul) relative to the described procedure. This results in measurable bactericidal activity with strongly bactericidal antisera only.
[c]The % clearance of GBM 80165 relative to PBS control from a 1:4 dilution of the respective antiserum.

Example 8

Further Studies Using N-Acyl Modified GBMP-TT Conjugates

A series of N-acyl modified GBM polysaccharides (N-propionyl GBMP (NPr), N-butanoyl GBMP (NBu), N-pentanoyl GBMP (NPe), and N-acryloyl GBMP (NAcryl) were synthesized essentially as previously described with the exception of using pH control to limit depolymerization of the polysaccharides. $^{1}H$- and $^{13}C$-NMR spectroscopy allowed complete identification of the modified polysaccharides, and it was determined that each polysaccharide was 100% derivatized. A series of oxidized polysaccharide fragments of the same molecular weight (11 KD) were generated based on SEC-HPLC profiled run on a standardized column. All of the conjugates were synthesized under the exact same conditions. Colorimetric analysis of the conjugates yielded the following sialic acid incorporation: NPr-28%, NBu-30%, NPe-18%, NAcryl-19%.

Mice were immunized with 2 $\mu$g of sialic acid/conjugate either in saline, absorbed onto aluminum hydroxide, or emulsified in RIBI's adjuvant. All of the conjugates were well tolerated in the mice with no visible signs of malaise.

ELISA titrations of the various antisera against homologous polysaccharide antigens are summarized in Table 1. The adjuvant producing the highest titers was found to be the RIBI's series increases from N-propionyl to N-pentanoyl substantiating previous findings using other hydrophobic adjuvant systems. In an adjuvant system such as alum, there does not appear to be a corresponding trend in titer. Specificity towards the immunizing polysaccharide also increases with increasing length of the acyl chain from N-propionyl to N-pentanoyl, most markedly in the RIBI series. (See Table 2). This result is also in accord with previous results which demonstrated the same trend. Despite the increase in titer and specificity, there is not an associated increase in activity against the native bacteria both in bactericidal and passive production assays. The N-Pr antiserum shows significantly higher bactericidal titers (14–25 times higher) at the 50 and 90% levels relative to the N-Bu and N-Pe antisera. Correspondingly, passive protection studies at different dilutions of antisera show significant clearance of the bacteria with the N-Bu and N-Pe at only the highest concentration, unlike the N-Pr antiserum which shows significant clearing even at 1:6 dilutions.

What is claimed is:

1. A modified group B meningococcal polysaccharide wherein the N-acetyl groups are substituted with an N-acyl derivative as in Formula (I):

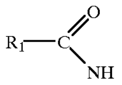

wherein $R_1$ is a $C_3$–$C_4$ unsaturated alkyl group.

2. The polysaccharide of claim 1 wherein $R_1$ is four carbons and has two non-adjacent double bonds.

3. The polysaccharide of claim 1 wherein $R_1$ is four carbons and has one double bond.

4. The polysaccharide of claim 1 wherein $R_1$ is three carbons.

5. The polysaccharide of claim 2 wherein $R_1$ is $CH_2$=CH—CH=CH—.

6. The polysaccharide of claim 3 wherein $R_1$ is $CH_2$=CH—$CH_2$—$CH_2$—.

7. The polysaccharide of claim 1 wherein the carbon most distant from the acyl carbon is bound through a double bond.

8. The polysaccharide of claim 7 wherein $R_1$ is four carbons.

9. The polysaccharide of claim 7 wherein $R_1$ is three carbons.

* * * * *